(12) United States Patent
Zannoli

(10) Patent No.: US 11,369,734 B2
(45) Date of Patent: Jun. 28, 2022

(54) METHOD FOR THE PREPARATION AND SUPPLY OF A DOSE OF A GASEOUS CONTRAST AGENT FOR ANGIOGRAPHY, AND DEVICE THAT ACTUALIZES SUCH A METHOD

(71) Applicant: ANGIODROID S.R.L., San Lazzaro di Savena (IT)

(72) Inventor: Sebastiano Zannoli, Bologna (IT)

(73) Assignee: ANGIODROID S.R.L.

( * ) Notice: Subject to any disclaimer, the term of this patent is extended or adjusted under 35 U.S.C. 154(b) by 608 days.

(21) Appl. No.: 15/989,935

(22) Filed: May 25, 2018

(65) Prior Publication Data
US 2018/0339101 A1    Nov. 29, 2018

(51) Int. Cl.
| | |
|---|---|
| *A61M 5/00* | (2006.01) |
| *A61M 5/148* | (2006.01) |
| *A61M 5/152* | (2006.01) |
| *A61M 5/172* | (2006.01) |
| *A61M 25/00* | (2006.01) |
| *A61M 39/22* | (2006.01) |

(52) U.S. Cl.
CPC ............ *A61M 5/007* (2013.01); *A61M 5/148* (2013.01); *A61M 5/1483* (2013.01); *A61M 5/152* (2013.01); *A61M 5/172* (2013.01); *A61M 25/00* (2013.01); *A61M 39/22* (2013.01); *A61M 2005/006* (2013.01); *A61M 2202/0225* (2013.01); *A61M 2205/3331* (2013.01)

(58) Field of Classification Search
CPC .... A61M 5/148; A61M 5/1483; A61M 5/007; A61M 5/152; A61M 39/22; A61M 2005/006; A61M 2202/0225; A61M 2205/3331
See application file for complete search history.

(56) References Cited

U.S. PATENT DOCUMENTS

| | | | | |
|---|---|---|---|---|
| 3,640,277 | A * | 2/1972 | Adelberg | A61M 5/1483 604/141 |
| 2008/0097323 | A1* | 4/2008 | Robertson | A61M 5/14593 604/142 |
| 2012/0226222 | A1* | 9/2012 | Zannoli | A61M 5/14593 604/23 |

FOREIGN PATENT DOCUMENTS

| | | | | |
|---|---|---|---|---|
| WO | WO-2005044343 A1 * | 5/2005 | | A61M 5/1483 |
| WO | WO-2009086684 A1 * | 7/2009 | | A61M 5/148 |

* cited by examiner

*Primary Examiner* — Nathan R Price
*Assistant Examiner* — Anh Bui
(74) *Attorney, Agent, or Firm* — Ware, Fressola, Maguire & Barber LLP

(57) ABSTRACT

A device for injecting contrast agent includes a supply line with a pressure regulator and leading to a soft injection bag in fluid communication with the supply line and with a catheter. The device also includes a pair of clamping plates acting on the injection bag and arranged on opposite sides of the injection bag. The clamping plates can be moves away from and close to each other. The device also includes a pair of inflatable compression bags. The compression bags are inflated with compressed air and act on corresponding clamping to plates to force the clamping plates to move close to each other and thus compress the injection bag. According to a method of the invention, the injection bag is filled from the source through the pressure regulator and a constant volume load container, and a contrast agent is supplied from the injection bag by gradually compressing the injection bag.

8 Claims, 3 Drawing Sheets

METHOD FOR THE PREPARATION AND SUPPLY OF A DOSE OF A GASEOUS CONTRAST AGENT FOR ANGIOGRAPHY, AND DEVICE THAT ACTUALIZES SUCH A METHOD

TECHNICAL FIELD

The present invention relates to the technical field concerning the production of equipment for radiographic examination.

In particular, the present invention refers to an apparatus for injection of a gaseous contrast agent into a blood vessel during an angiographic examination, and more precisely consists in a method for preparation and supply of a predefined amount of the above mentioned gaseous contrast agent into a catheter, and from there to the vessel subjected to the angiographic test; the invention includes also a device that implements the above method.

BACKGROUND ART

It is known that an angiographic examination includes injection of a contrast agent into a vascular cavity (artery or vein) and recording of radiological images of the area being examined. The diagnostic purpose of angiography is to examine and visualize the possible presence of structural anomalies of the vascular cavity being examined, including narrowing (stenosis) and dilatations (aneurysms) of the vessel lumen. The technique is widely applied to cardiopathic and vasculopathic patients, due to the particularly high spatial resolution and diagnostic sensitivity that can be obtained.

Solutions containing iodine in liquid phase are currently very often used as a contrast agent. Mixed with blood, they significantly modify its response to the passage of the radiation, and allow obtainment of homogeneous and well defined radiographic images of the area being examined.

Technical Problem

The use of iodized contrast agent in angiographic techniques is mainly limited by problems of subjective intolerance to the agent, especially in the presence of some pathological conditions (diabetic patients, nephropathic patients, etc.). Moreover, the incidence of these diseases is rapidly growing due to the increasing average age of patients.

To overcome the drawbacks of angiographic techniques using the iodized agent, the use of carbon dioxide ($CO_2$) as an alternative contrast agent has been established. This gas is particularly suitable for this purpose because, once injected into the vessel, it allows obtainment of an excellent radiographic visualization of the injection area and does not cause problems of tolerance and elimination, since it is quickly and completely eliminated by the lungs.

The first injection devices used in angiographic examination with $CO_2$ were manually operated, and basically used syringes filled with gas, which were activated directly by the operator during the injection. Using these syringes, the gas was injected directly into the site by means of a catheter previously placed in the area of interest. The disadvantage of these systems derives from the fact that they do not ensure a complete and certain absence of air in the injection circuit, and expose the patient to the risk of air embolism.

Subsequently, injection devices, originally designed for use with liquid contrast agents, have been modified and adapted for this purpose, in order to make them suitable for gas injection.

However, the various manual or automatic instrumental solutions that have been proposed do not resolve a fundamental problem, which affects the diagnostic result, namely, control of the gas infusion rate and preparation of the quantity of gas to be injected. On the other hand, like with the injectors of contrast agents in liquid phase, due to the compressible nature of gas, the simple regulation of the advancing speed of the piston of the injector does not allow an adequate control of the injection flow. Moreover, the injection pressure cannot be reliably controlled, since the variations of volume imparted to the injection syringe correspond, due to the high compressibility of the gas and differences in emptying speed, to as many variations in pressure, which are, inter alia, unpredictable due to the variability of the specific injection conditions.

The obtained result is a non homogeneous and difficult to control opacification of the vascular cavity to be observed. This can make the diagnosis of possible pathologies difficult and sometimes with little precision and reliability.

The above described devices are also rather complicated and expensive.

The International Patent Application PCT published under No. WO2011/061614 in the name of Spark S.r.l. describes a device for injection of $CO_2$ that tackles the above listed problems and gives significant improvements in the regulation of contrast media flow during injection. The device includes a pair of soft bags, which have at least one common wall. A first bag is connected to the devices for supplying and dosing the contrast agent and, before the injection is carried out, it receives the dose of $CO_2$ to be injected from these devices. A second bag, with a volume significantly bigger with respect to the first bag, is then inflated with air and brought to the injection pressure. In this way, the action of the second bag on the first one makes the latter compress $CO_2$ to the same pressure. The two bags are enclosed within a rigid, generally cylindrical container, which defines a constant maximum overall volume for the two bags.

Afterwards, the first bag is brought into communication with a catheter, whose opposite end was previously inserted into the vessel to be visualized. In this way the pressure inside the first bag remains substantially constant, as it is imposed by the pressure of air contained in the second bag. Therefore, also the flow of injected $CO_2$ is substantially constant.

Moreover, the structure of the above described device makes overpressures virtually impossible during the injection of the contrast agent, and is capable of considerably reducing the possibility of contamination of the contrast agent during the preparation of the device.

However, the above described double-bag device may present one drawback, and an inherent operational limitation generated by the structure of the device. These drawback and limitations are, however, the same as those of other known devices.

The above mentioned drawback derives from the fact that, due to the geometry of the rigid container that encloses the bags or other more or less random factors, it may happen that the bag containing the $CO_2$ is not able to empty completely. This happens, for example, if the bag containing the $CO_2$ is pushed towards a corner of the container. Thus, it is not sure that the whole dose of $CO_2$ is injected.

The operational limit inherent to the above described device derives from a rather long time necessary to prepare the $CO_2$ injection operation. In particular, the time necessary for the syringe to take the gas dose and then release it into the injection bag is long. This is caused by the fact that the plunger of the syringe, which is driven by a stepper motor, cannot be moved at high speeds, in order to avoid breaking of the drive mechanisms and seals of the plunger. This last event, in particular, could make a part of the gas disperse into the atmosphere, distorting its dosage, or make air enter the syringe, with the consequent contamination of the gas subsequently injected into the patient.

OBJECTS OF THE INVENTION

One object of the present invention is to propose a device for preparation and regulation of the flow of a gaseous contrast agent for angiography, of the type provided with a bag, or other soft container, aimed at containing the dose of $CO_2$ to be injected, capable of ensuring rapid attainment of the desired dose, and complete discharge of the aforesaid dose maintaining a flow of the contrast agent to the vessel subjected to the angiographic examination substantially constant.

Another object of the invention is to propose a device aimed at implementing the above mentioned method, which regulates the flow of the gaseous contrast agent and ensures the complete emptying of the container of the dose of $CO_2$ to be injected, and thus the administration of the entire dose provided for the angiographic examination with the best supply methods.

A further object of the invention is to propose a device for the regulation of the flow capable of administering the dose of $CO_2$ in an absolutely safe way.

SUMMARY OF THE INVENTION

The above mentioned objects are wholly obtained, in accordance with the content of the claims and with preferred but not exclusive embodiments of the invention, by a method, and device that carries it out, for preparation and supply of a dose of a gaseous contrast agent for angiography, which operate in an apparatus for the injection of said contrast agent.

The device includes: a supply line for fluid, in particular gas; a pressure regulator; a soft injection bag in fluid communication with the supply line and a catheter.

The device includes also pressing means, which include a pair of clamping plates acting on the injection bag, arranged on opposite sides with respect to the injection bag, moveable away from and close to each other, and including also a pair of compression bags, which can be inflated with compressed air. The compression bags are designed to act on the corresponding clamping plates so as to force them to move close to each other and thus compress the injection bag.

According to the method of the invention, the injection bag is filled to from a load container of constant volume, in turn filled from the source through the pressure regulator, and the contrast agent is delivered from the injection bag contained between the two plates moving close to each other, in turn forced by the compression bags inflated with compressed air.

BRIEF DESCRIPTION OF THE DRAWINGS

The characteristics of the invention, as they become evident from the claims, are pointed out in the following detailed description, with reference to the enclosed drawings, in which:

DETAILED DESCRIPTION

Figure 1:
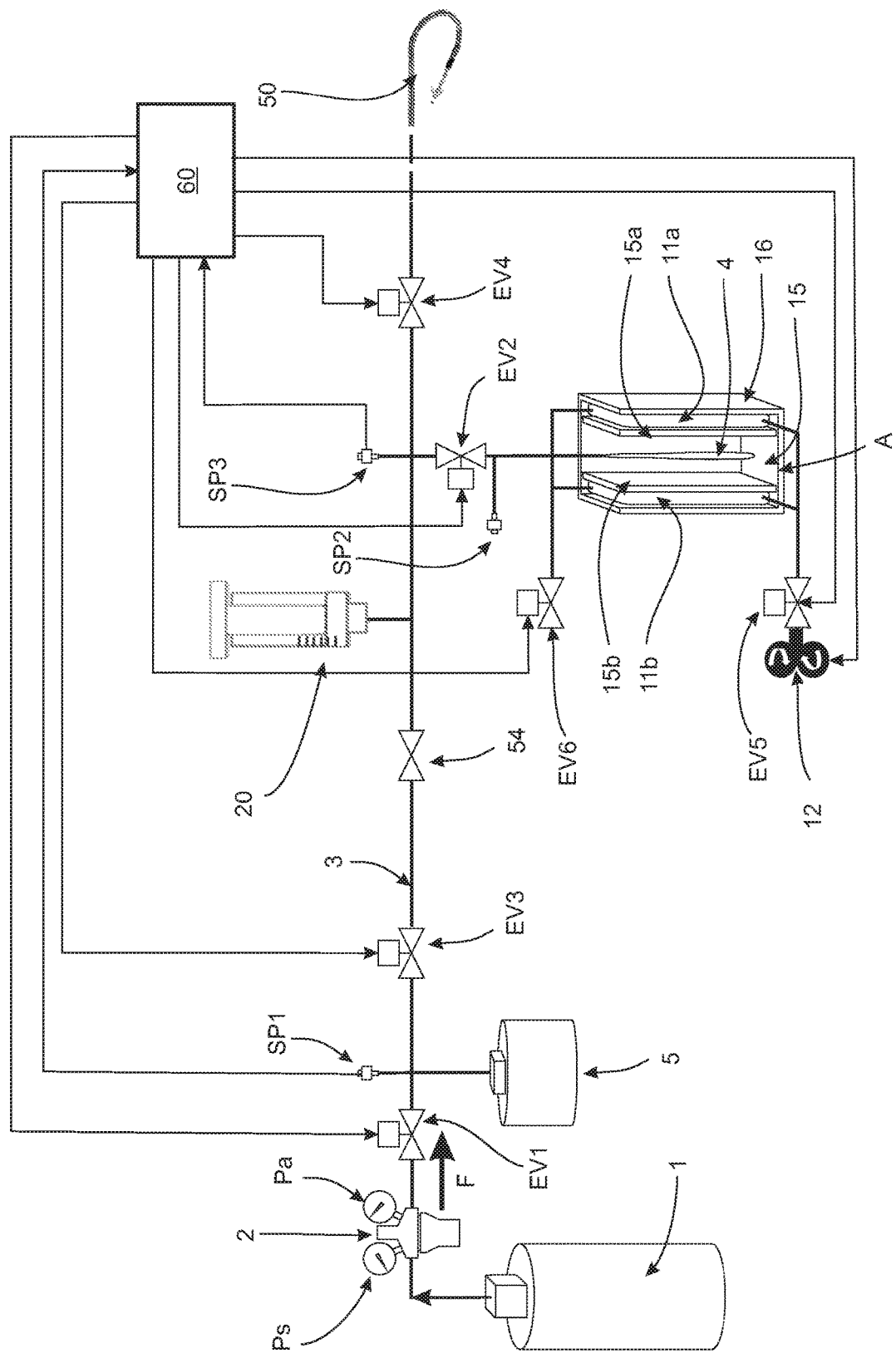
FIG. 1 is a schematic view of a device for preparation and supply of a gas contrast agent made according to the invention, in an initial situation.

With reference to an embodiment shown in FIG. 1, a device is shown, as a whole, for preparation and regulation of a contrast agent in angiography, by means of a catheter 50, of known type, illustrated schematically in the figures, since its structure and functions are not strictly relevant to the invention.

The device of FIG. 1 is a part of an apparatus for the injection of predefined doses of a gaseous contrast agent, typically consisting of carbon dioxide ($CO_2$), but also usable with any gaseous contrast agent suitable for application in endovascular diagnostics. The apparatus includes, inter alia, a computerized control unit 60, intended for managing the functions of the apparatus, provided with appropriate processing, storage and communication structures, as well as programs dedicated to the execution of the functions of the same.

In the following description, reference will be made, by way of example, to the administration of carbon dioxide as a contrast agent. The structure of the injection apparatus will not be described in further detail, since it is not relevant to the invention.

The device of FIG. 1 is connected to a source 1 aimed at supplying carbon dioxide of adequate chemical purity at a predetermined pressure $P_s$, with the interposition of a pressure regulator 2; which, in turn, supplies at the output carbon dioxide at a substantially constant supply pressure $P_a$, lower than the inlet pressure $P_s$, and typically of about 0.5 bar. If necessary, an appropriate filter is also provided to ensure the purity of the supplied carbon dioxide. The pressure regulator 2 is connected to a supply line 3, intended for delivering the contrast agent to the components of the device of FIG. 1.

The source 1 can be formed either by a tank under pressure or the terminal of a fixed gas distribution system, depending on the logistic situation of use of the device 100. The predetermined supply pressure $P_s$ in the case of a tank is typically about 60 bar, while in the case of a distribution system the pressure can also be very different.

In the embodiment of FIG. 1, the device includes a first shut-off solenoid valve EV1, situated on the supply line 3 directly downstream of the pressure regulator 2 and designed to interrupt or allow the flow of gas from the above regulator 2 to the supply line 3. A first pressure sensor SP1, connected to the control unit 60, is provided directly downstream of the first solenoid valve EV1.

The device of FIG. 1 includes also a soft injection bag 4, having a predefined capacity, sufficient for injection of a contrast agent. The injection bag 4 is connected in an interruptible way to the supply line 3, with the interposition of a second interception solenoid valve EV2, and is intended for receiving a dose of contrast agent to be injected during the execution of the angiography, to release it on command to the aforementioned catheter 50. The material of which the injection bag 4 is made, is completely impermeable, both to the carbon dioxide at the outlet and to the atmospheric gases at the inlet, and is soft but not yielding, at least at the operating pressures for the purposes of the invention.

The injection bag 4 is also set in interruptible fluid communication with catheter 50, which, in the described embodiment, is connected to the supply line 3 by means of the aforementioned second shut-off valve EV2 and an output shut-off valve EV4 situated directly upstream of the catheter 50 (FIG. 1). A second pressure sensor, or injection pressure sensor, SP2, is provided directly at the outlet of the injection bag 4, to allow the control unit 60 to monitor the pressure inside the bag 4. Not shown, to avoid cluttering the figure, is a signal line back to the control unit, similar to that shown for the first pressure sensor SP1.

The device of the figure comprises also pressing means, designed to act on the injection bag 4 to define the way in which the contrast agent is put therein and delivered to the catheter 50. The pressing means, in particular, include a clamping device 15 acting on the injection bag 4, which is provided with a pair of opposite clamping elements, respectively a first clamping element 15a and a second clamping element 15b, in the illustrated embodiment consisting of a pair of plates of rigid material.

The first plate 15a and second plate 15b move away from and toward each other. In the described embodiment, they are parallel to each other and made to slide in a manner known to a person skilled in the art, for example by mounting them on slides. The configuration of plates 15a, 15b is such that, when they are in a maximum distance position A (FIGS. 1 and 2), or rest position, they do not interfere with the injection bag 4 (or they do it in an insignificant way), which can then assume a totally loose configuration, while, when they are in a maximum approach position B (FIG. 3), they squeeze the injection bag 4 until its opposite walls join, i.e., essentially, until it collapses completely.

The pressing means include also a pair of compression bags, a first compression bag 11a and a second compression bag 11b, made of soft, elastic and airtight material. Each compression bag is installed directly behind a corresponding plate 15a, 15b. The compression bags 11a, 11b are destined to be filled with pressurised air to push the plates 15a, 15b and force them to the closest approach position (see FIGS. 2 and 3).

Supply means for compressed air 12 are provided to inflate the compression bags 11a, 11b, thus increasing their volume until the above described effect is achieved. The supply means comprise, in particular, a compressor and a non-return valve EV5, which can be operated automatically or controlled by the control unit 60. An additional solenoid valve EV6, controlled by the control unit 60, is provided on an outlet duct, connected to the compression bags 11a, 11b, to expel the air from the bags and allow them to empty.

A rigid container 16 suitably shaped encloses the pressing means 10, so as to provide support for the compression bags 11a, 11b, plates 15a, 15b and injection bag 4, and to act as a shoulder for the compression bags 11a, 11b, as will be evident in the following description.

There are also means, not illustrated as immediately understandable, designed to bring plates 15a, 15b back to the rest position A, once the stress by the compression bags 11a, 11b is over, that is, when the air contained therein is expelled into the atmosphere. For example, they may consist of one or more return springs, which can be loaded by the expansion of the compression bags 11a, 11b.

According to a different embodiment, usually preferred because of its constructive simplicity, the plates 15a, 15b can also be mounted hinged together at one side, and in this case they move toward and away from each other by rotation about the hinge axis. Such a configuration is clearly understandable, but it has not been illustrated in the figures and will not be described in further detail. In this embodiment, the plates 15a, 15b can be placed in the apparatus for the administration of the contrast agent, mirrored symmetrically with respect to a vertical plane. In this way, when they are in the open position, the plates are in a stable balance situation and once the compression bags 11a, 11b have been emptied, the plates naturally tend to return to the open position. Therefore, the above-mentioned return springs can be avoided, thus simplifying the construction of the device.

According to a further embodiment, only one of the above mentioned plates, for example the first plate 15a, can be made mobile as described above, while the other can be mounted fixed, or can be omitted. In this case, the second clamping element 15b can be a wall of the rigid container 16. In this further embodiment, only one compression bag 11a is provided to act on the movable plate 15a in the already described ways.

In any case, for simplicity of presentation, the operating method according to the invention will be described in the following with reference to the embodiment of the device illustrated in the figures, i.e., with the pressing means 10 that include two plates 15a, 15b mounted parallel to each other and both mobile.

A constant volume container 5, set in fluid communication with the supply line 3, is also provided between the first shut-off valve EV1 and second shut-off valve EV2. A further third shut-off valve EV3 is provided on the same line 3 downstream of the load container 5 of constant volume.

A passive flow regulator 54 of known type is provided on the supply line 3, between the above mentioned second shut-off valve EV2 and third shut-off valve EV3. The regulator 54 is essentially provided with a narrowing, which may be adjusted if necessary, and is intended for preventing excessive gas flow, when there are big pressure differences between the container 5 and injection bag 4, for example when the container 5 is at its maximum pressure and the injection bag is completely empty.

The load container 5 is made of a suitable rigid material, has a volume significantly bigger than the injection bag 4, and is destined to contain the contrast agent at a pressure, which is likewise higher than the loading pressure of the injection bag 4, as will be described in detail below.

The above mentioned first SP1 sensor, or load sensor, is designed to detect the pressure on the supply line 3 at the load container 5. The above mentioned first pressure sensor SP1 allows therefore to monitor the pressure inside the above mentioned container 5.

A further, third pressure sensor SP3 is provided upstream of the output solenoid valve EV4 to monitor the output pressure to the catheter 50.

A purge syringe 20, provided on the supply line 3, between the second solenoid valve EV2 and third solenoid valve EV3, is intended to take a quantity of contrast agent, before carrying out the angiographic examination, and inject it directly to the catheter 50, to free it from any blood reflux and place the supply device in an optimal operating condition. The purging operation is not strictly pertinent to the invention, and therefore will not be described in further detail.

According to the method for preparation and supply of a dose of gaseous contrast agent, and in particular carbon dioxide, according to the invention, managed by the control unit 60 by means of a special software program, the source 1 of carbon dioxide is first prepared for the supply of $CO_2$. The gas is supplied to the supply line 3 through the pressure regulator 2 and the first solenoid valve EV1 (arrow F of FIG. 1). The latter is in a closed position, so there is no $CO_2$ supply downstream thereof.

According to a preferred embodiment of the method of the invention, to inject the predetermined quantity of carbon dioxide into the vessel, this quantity is put into the injection bag 4. When the first solenoid valve EV1 and third solenoid valve EV3 are closed, the communication between the injection bag 4 and catheter 50 is interrupted, closing the output solenoid valve EV4; moreover, if necessary, the communication between the pressure regulator 2 and injection bag is interrupted by closing the second solenoid valve EV2.

Figure 2:
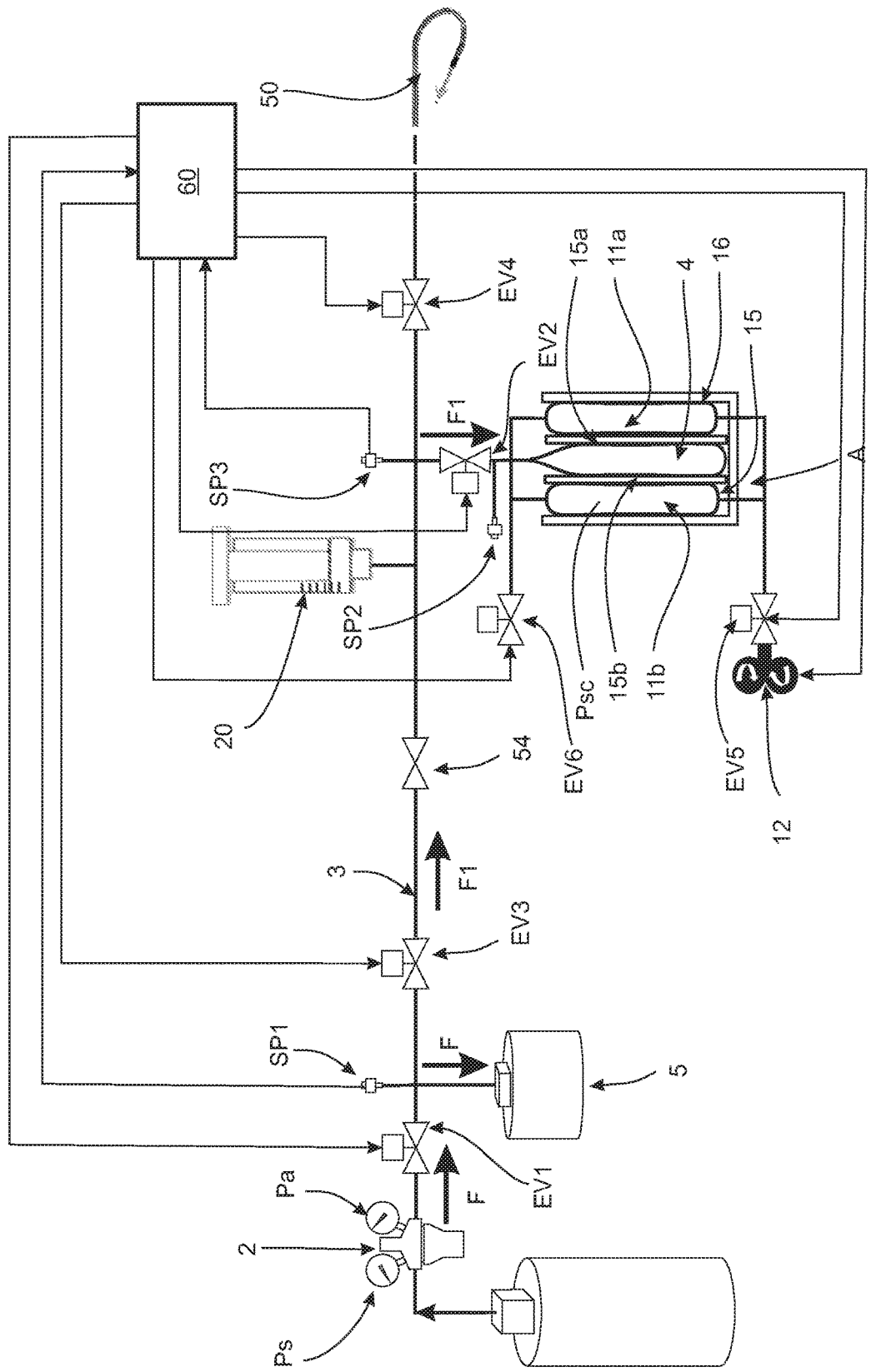
FIG. 2 is a schematic view of the device of FIG. 1 while being filled with the gas contrast agent.
Figure 3:
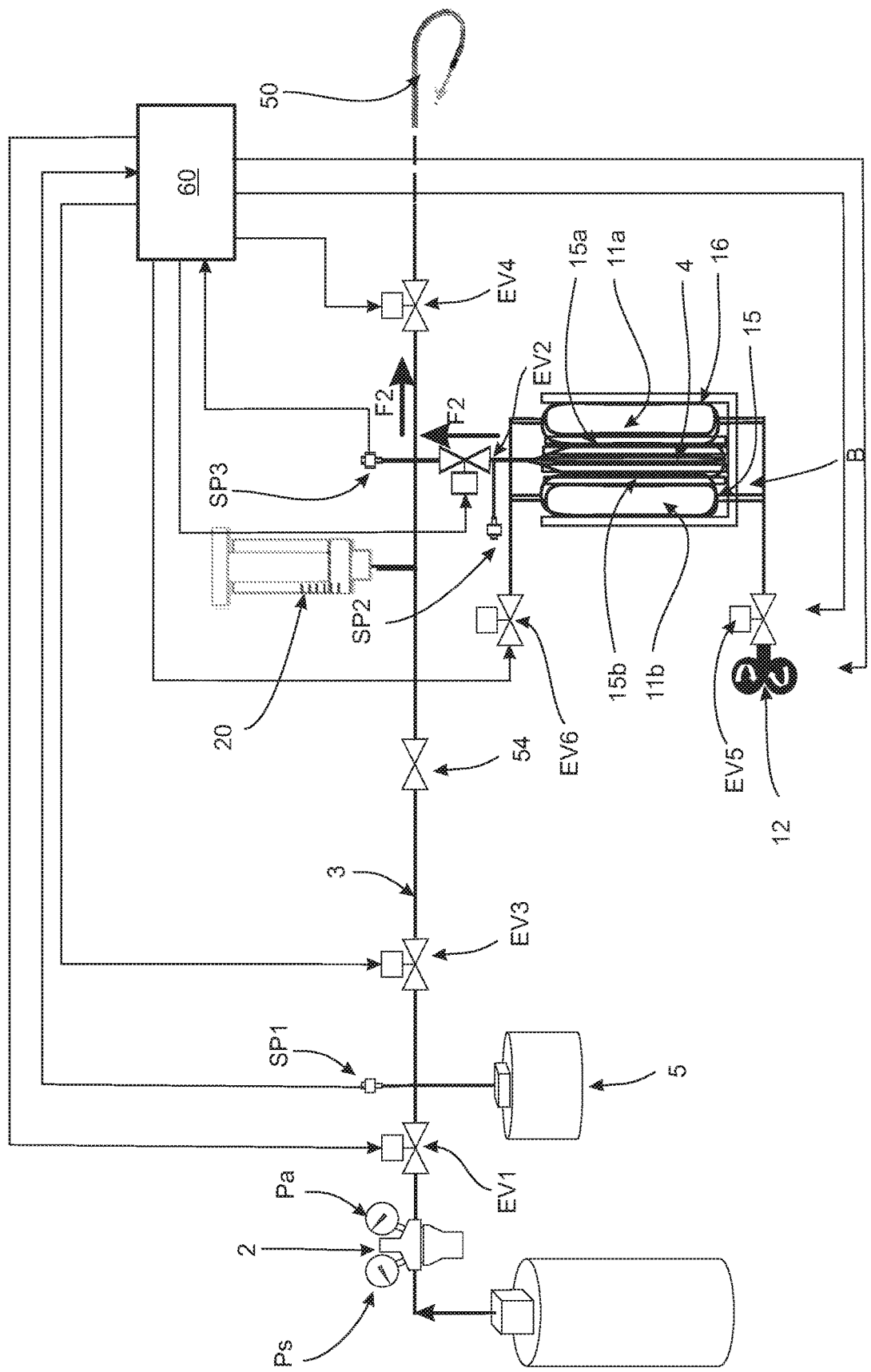
FIG. 3 is the same view as the previous figures, with the device during the emptying of the injection bag.

Carbon dioxide is then introduced into the load container 5, opening the first solenoid valve EV1 until a load pressure reaches a value Pc, measured by the compensation pressure sensor SP1, which is significantly higher than the maximum injection pressure to be obtained (flow indicated with the arrow F in FIG. 2). For example, a 150 mmHg pressure seems to be adequate for the subsequent requirements of loading times, which are described below.

In the next phase, carbon dioxide is injected into the injection bag 4, opening the second solenoid valve EV2 and third solenoid valve EV3 until the dose of contrast agent to be injected into the vessel in that operation is reached (flow indicated with F1 in FIG. 2). Since the values of pressure inside the load container 5 and injection bag 4 are known, the dose of contrast agent in the latter is simply measured by opening the second solenoid valve EV2 and third solenoid valve EV3, and monitoring the pressure read by the sensor SP1. For this purpose, according to the ideal gas law, the desired number of moles of $CO_2$ that are transferred to the injection bag 4 can be calculated on the basis of a given pressure drop in the load vessel 5, detected by the sensor SP1. Therefore, the opening time of solenoid valves EV2, EV3 depends on the value of the load pressure Pc in the container 5 and on the dose of contrast agent to be injected. When the loading operation is completed, a value of the injection pressure Pq reached inside the injection bag is significantly lower than the loading pressure Pc, for example 50-55 mmHg. By defining appropriately the difference between the loading pressure Pc and the injection pressure Pq, it is possible to obtain a sufficiently short filling time for the injection bag 4.

Consequently, the communication between the injection bag 4, pressure regulator 2 and load container 5 is interrupted by closing the second solenoid valve EV2 and, if necessary, the first solenoid valve EV1.

The contrast agent is then injected into the vessel. After the introduction of the catheter 50 in situ, the compressor 12 is activated to introduce compressed air into the compression bags 11a, 11b until a value of emptying pressure Pss is reached, which depends on the type of body area to be examined, on the patient's systemic pressure and on the parameters of the used catheter. Typically this value is between about 100 and 600 mmHg, but other values can be provided depending on particular application requirements.

Optionally, before or during loading of the dose of contrast agent into the injection bag 4, the compression bags 11a, 11 b can be partially inflated beforehand to bring the plates 15a, 15b to an intermediate position and accelerate the subsequent emptying of the injection bag 4.

The second solenoid valve EV2 and output solenoid valve EV4 are then opened, and carbon dioxide flows from the injection bag 4 towards the catheter 50 due to the effect of the gas pressure and the thrust carried out by the plates 15a, 15b pushed by the compression bags 11a, 11 b. The compression action performed by the compression bags makes the plates 15a, 15b move close to each other while the injection bag 4 is emptying, and is maintained until the position of closest approach B of the compression bags (FIG. 3) is reached and the injection bag 4 is completely emptied.

The effect of the compression plates and bags, fundamental for the purposes of the present invention, is a regulation of the flow of carbon dioxide and ensure the complete emptying of the injection bag 4. This last effect, in particular, is certainly obtained because the plates 15a, 15b are brought practically into contact with each other.

In one variant of the method, starting from an intermediate moment during the supply phase of the contrast agent, the pressing means are activated again, operating the compressor 12 to inject new compressed air into the compression bags 11a, 11b, and obtain an additional thrust on the plates 15a, 15b, and then further facilitate the emptying of the injection bag 4.

When the injection operation is completed, the air is expelled from the compression bags 11a, 11 b, by opening the solenoid valve EV6. The plates 15a, 15b are brought back to their rest position A by the return springs.

The advantages of the present invention derive primarily from the rapid achievement of the desired dose of contrast agent, due to the fact that the injection bag 4 is loaded from a high-pressure load container 5, but is not dangerous for the patient.

In addition, a further advantage derives from the fact that the above dose is completely removed from the injection bag 4, while maintaining also substantially constant a flow of contrast agent to the vessel subjected to the angiographic examination.

The whole injection operation is also achieved with maximum safety due to the design of the compensation container 5.

It is understood that what above has been described is a purely non-limiting example. Therefore, possible changes and variants of the invention are considered within the protective scope granted to the is present method, as described above and claimed below.

The invention claimed is:

1. Apparatus for preparation and supply of a dose of gaseous contrast agent for angiography by injecting said contrast agent, said apparatus comprising:
   a constant volume load container, set in interruptible fluid communication with a source and set in interruptible fluid communication with a soft injection bag, with flow interrupting devices operated independently and aimed at establishing and interrupting fluid communication between said source and said constant volume load container so as to fill said constant volume load container from said source with flow to the soft injection bag interrupted, and between said constant volume load container and said soft injection bag so as to fill said soft injection bag from said constant volume load container with flow from the source interrupted and so as to interrupt flow from the constant volume load container when the soft injection bag is full;
   a supply line, set in fluid communication with the constant volume load container, for supplying said contrast agent at a supply pressure that is substantially constant and lower than a pressure provided by said source, wherein
   said soft injection bag is set in interruptible fluid communication with said supply line, wherein said injection bag is also set in interruptible fluid communication with a catheter, and wherein said soft injection bag is for receiving a dose of said contrast agent coming from said constant volume load container so as to release said contrast agent on command into said catheter and inject the dose of said contrast agent into a vascular cavity via said catheter;

wherein said apparatus further comprises pressing means comprising in turn a clamping device of said injection bag, said clamping device provided with at least a pair of opposed clamping elements, namely a first clamping element and a second clamping element, arranged on opposite sides with respect to the injection bag, at least one of said clamping elements moveable away from and toward the other clamping element, said pressing means also comprising a compression apparatus for acting in response to said command on at least one corresponding clamping element so as to force it close to the opposed clamping element until the soft injection bag is completely emptied of the dose.

2. The apparatus according to claim 1, wherein said compression apparatus includes at least a compression bag, which is inflatable with compressed air provided on said command by a compressed air supply.

3. The apparatus according to claim 1, wherein, in said clamping device, said clamping elements include two opposed plates, namely a first plate and a second plate, both moving close to and away from each other, and hinged to each other at a respective end, and wherein two compression bags, namely a first bag and a second bag are provided, each compression bag for pushing on a respective plate.

4. The apparatus according to claim 1, wherein, in said clamping device, said clamping elements are formed by two opposed rigid plates, namely a first rigid plate and a second rigid plate, said opposed rigid plates moving close to and away from each other, and mounted parallel to each other, and wherein two compression bags, namely a first compression bag and a second compression bag, are provided, respectively, each compression bag for pushing on a respective rigid plate.

5. The apparatus according to claim 1, further including an injection pressure sensor (SP2) for measuring a pressure of the contrast agent in said soft injection bag.

6. The apparatus according to claim 1, further comprising a passive flow regulator set in said supply line to regulate flow between said constant volume container and said soft injection bag so as to prevent excessive gas flow when initially filling the soft injection bag when the load container is at its maximum pressure and the soft injection bag is completely empty.

7. The apparatus according to claim 6, further comprising a first pressure sensor to sense pressure in said constant volume load container and a second pressure sensor (SP2) for measuring an injection pressure of the contrast agent in said soft injection bag.

8. The apparatus according to claim 5, further comprising a passive flow regulator set in said supply line to regulate flow between said constant volume container and said soft injection bag so as to prevent excessive gas flow upon commencement of a filling of the soft injection bag when the load container is at its maximum pressure and the soft injection bag is completely empty.

\* \* \* \* \*